United States Patent
Hasegawa

(10) Patent No.: US 12,161,887 B2
(45) Date of Patent: Dec. 10, 2024

(54) RADIATION THERAPY APPARATUS AND RADIATION THERAPY METHOD

(71) Applicant: CANON MEDICAL SYSTEMS CORPORATION, Tochigi (JP)

(72) Inventor: Shinji Hasegawa, Nasushiobara (JP)

(73) Assignee: CANON MEDICAL SYSTEMS CORPORATION, Tochigi (JP)

( * ) Notice: Subject to any disclaimer, the term of this patent is extended or adjusted under 35 U.S.C. 154(b) by 421 days.

(21) Appl. No.: 17/454,662

(22) Filed: Nov. 12, 2021

(65) Prior Publication Data

US 2022/0152424 A1 May 19, 2022

(30) Foreign Application Priority Data

Nov. 13, 2020 (JP) ................................ 2020-189095

(51) Int. Cl.
*A61N 5/10* (2006.01)
(52) U.S. Cl.
CPC .......... *A61N 5/1067* (2013.01); *A61N 5/1045* (2013.01); *A61N 2005/1062* (2013.01); *A61N 5/1081* (2013.01)
(58) Field of Classification Search
None
See application file for complete search history.

(56) References Cited

U.S. PATENT DOCUMENTS

| | | | | |
|---|---|---|---|---|
| 9,764,162 B1 * | 9/2017 | Willcut | .................. | G06T 7/0014 |
| 10,071,264 B2 * | 9/2018 | Liger | .................... | A61N 5/1067 |
| 10,485,993 B2 * | 11/2019 | Goer | ..................... | A61N 5/1049 |
| 10,603,514 B2 * | 3/2020 | Grittani | ................ | A61N 5/1075 |
| 10,814,144 B2 * | 10/2020 | Khuntia | ............... | A61N 5/1045 |
| 10,843,011 B2 * | 11/2020 | Trail | ..................... | H01J 37/073 |
| 11,173,325 B2 * | 11/2021 | Parry | ....................... | A61K 9/51 |

(Continued)

FOREIGN PATENT DOCUMENTS

| | | |
|---|---|---|
| JP | H07-275381 A | 10/1995 |
| JP | 2017-189527 A | 10/2017 |

(Continued)

OTHER PUBLICATIONS

Favaudon et al., "Ultrahigh dose-rate FLASH irradiation increases in differential response between normal and tumor tissue in mice", Science Translational Medicine, vol. 6, issue 245, 2014, 10 pages.

(Continued)

*Primary Examiner* — Thomas R Artman
(74) *Attorney, Agent, or Firm* — Oblon, McClelland, Maier & Neustadt, L.L.P.

(57) ABSTRACT

A radiation therapy apparatus according to an embodiment includes a radiation generator and processing circuitry. The radiation generator is configured to emit radiation having an ultrahigh dose rate. The processing circuitry is configured to measure a dose of the radiation emitted from the radiation generator over a period of time. The processing circuitry is configured to calculate an accumulated dose and a dose rate of the radiation emitted from the radiation generator, on a basis of the dose of the radiation measured over the period of time. The processing circuitry is configured to control the radiation generator, on a basis of the dose of the accumulated dose and the dose rate.

8 Claims, 7 Drawing Sheets

(56) References Cited

U.S. PATENT DOCUMENTS

| | | | |
|---|---|---|---|
| 11,534,625 B2 * | 12/2022 | Khuntia | A61N 5/1045 |
| 2016/0287905 A1 * | 10/2016 | Liger | A61N 5/1067 |
| 2019/0022411 A1 | 1/2019 | Parry et al. | |
| 2019/0022422 A1 | 1/2019 | Trail et al. | |
| 2019/0054318 A1 * | 2/2019 | Goer | A61N 5/1067 |
| 2019/0329071 A1 | 10/2019 | Grittani et al. | |
| 2020/0282232 A1 * | 9/2020 | Khuntia | A61N 5/1031 |
| 2021/0016108 A1 * | 1/2021 | Khuntia | A61N 5/1043 |
| 2022/0152424 A1 * | 5/2022 | Hasegawa | A61N 5/1048 |
| 2022/0323793 A1 * | 10/2022 | Brooks | A61N 5/1071 |
| 2023/0125147 A1 * | 4/2023 | Khuntia | A61N 5/103 |
| | | | 378/65 |

FOREIGN PATENT DOCUMENTS

| | | |
|---|---|---|
| WO | WO 2015/155868 A1 | 10/2015 |
| WO | WO 2020/185544 A1 | 9/2020 |

OTHER PUBLICATIONS

Vozenin et al., "The advantage of FLASH radiotherapy confirmed in mini-pig and cat-cancer patients", American Association for Cancer Research, 2018, 22 pages.

Buonanno et al., "Biological effects in normal cells exposed to FLASH dose rate protons", Radiotherapy and Oncology, 2019, 5 pages.

Japanese Office Action dated Jun. 12, 2024, issued in Japanese Patent Application No. 2020-189095 (with English translation).

* cited by examiner

RADIATION THERAPY APPARATUS AND RADIATION THERAPY METHOD

CROSS-REFERENCE TO RELATED APPLICATIONS

This application is based upon and claims the benefit of priority from Japanese Patent Application No. 2020-189095, filed on Nov. 13, 2020; the entire contents of which are incorporated herein by reference.

FIELD

Embodiments described herein relate generally to a radiation therapy apparatus and a radiation therapy method.

BACKGROUND

In recent years, for radiation therapies, a FLASH irradiation method is known by which radiation having an ultra-high dose rate, which is hundreds to thousands times higher than a dose rate used in normal radiation therapies, is emitted onto a radiation irradiated region. The FLASH irradiation method is attracting attention because the method is able to prevent the occurrence of disturbances in normal tissues, while keeping advantageous effects on a target tissue subject to the radiation therapy.

DETAILED DESCRIPTION

According to an embodiment, a radiation therapy apparatus includes a radiation generator and processing circuitry. The radiation generator is configured to emit radiation having an ultrahigh dose rate. The processing circuitry is configured to measure a dose of the radiation emitted from the radiation generator over a period of time. The processing circuitry is configured to calculate an accumulated dose and a dose rate of the radiation emitted from the radiation generator, on a basis of the dose of the radiation measured over the period of time. The processing circuitry is configured to control the radiation generator, on a basis of the dose of the accumulated dose and the dose rate.

Embodiments of a radiation therapy apparatus and a radiation therapy method of the present disclosure will be explained in detail, with reference to the accompanying drawings. The radiation therapy apparatus and the radiation therapy method of the present disclosure are not limited to the embodiments described below. Further, it is possible to combine any of the embodiments with another embodiment or conventional techniques as long as no conflict occurs in the processing.

First Embodiment

Figure 1:
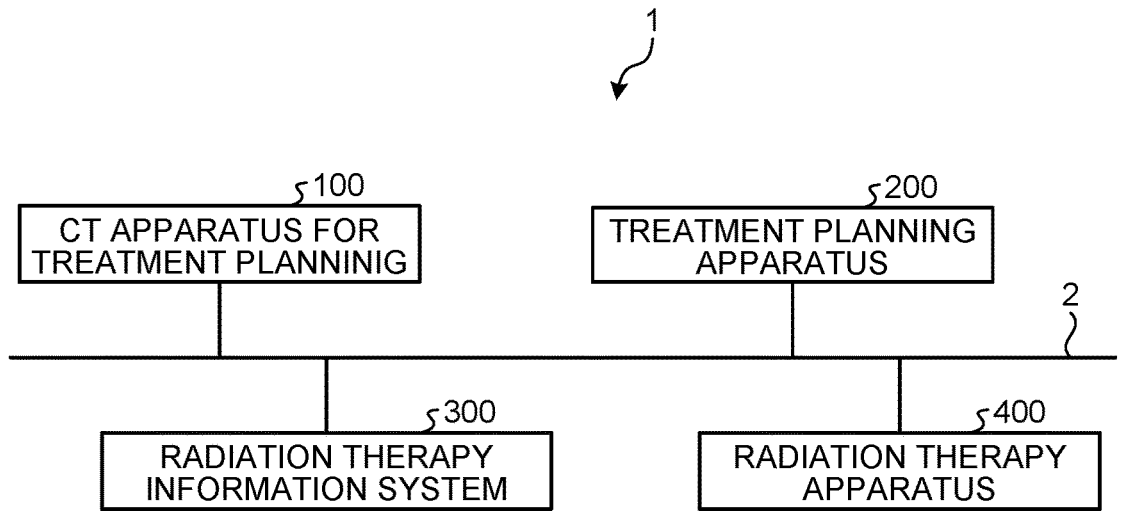
FIG. 1 is a diagram illustrating an exemplary configuration of a radiation therapy system according to a first embodiment.

To begin with, a radiation therapy system including a radiation therapy apparatus according to the present embodiment will be explained. FIG. 1 is a diagram illustrating an exemplary configuration of a radiation therapy system 1 according to a first embodiment. As illustrated in FIG. 1, the radiation therapy system 1 according to the first embodiment includes a Computed Tomography (CT) apparatus for treatment planning 100, a treatment planning apparatus 200, a radiation therapy information system 300, and a radiation therapy apparatus 400. The CT apparatus for treatment planning 100, the treatment planning apparatus 200, the radiation therapy information system 300, and the radiation therapy apparatus 400 are communicably connected to one another via a network 2. The configuration illustrated in FIG. 1 is merely an example, and possible embodiments are not limited to this configuration. For example, the radiation therapy system 1 may include other various types of apparatuses, devices, and systems.

The CT apparatus for treatment planning 100 includes a gantry, a table device having a tabletop, and a console and is configured to acquire CT image data rendering a treatment target site (e.g., a tumor) of a treatment subject lying on the tabletop and to further transmit the acquired CT image data to the treatment planning apparatus 200. More specifically, the CT apparatus for treatment planning 100 is configured to acquire projection data while causing an X-ray tube and an X-ray detector included in the gantry to rotate around the treatment subject and to reconstruct three-dimensional CT image data on the basis of the acquired projection data. In this situation, the tabletop of the treatment planning CT apparatus 100 has a flat shape, similarly to a tabletop of the radiation therapy apparatus.

In the present embodiment, only the CT apparatus for treatment planning 100 is presented as an apparatus configured to acquire the image data used for the treatment planning; however, possible embodiments are not limited to this example. For instance, a Magnetic Resonance Imaging (MRI) apparatus for treatment planning or an X-ray diagnosis apparatus or an ultrasound diagnosis apparatus capable of outputting a three-dimensional image may be configured to acquire the three-dimensional image data used for the treatment planning.

The treatment planning apparatus 200 is configured to make a treatment plan of a radiation therapy to be performed by the radiation therapy apparatus 400, by using the three-dimensional CT image data of the treatment subject acquired by the CT apparatus for treatment planning 100. For example, the treatment planning apparatus 200 is configured to identify the position of the treatment target site in the body of the treatment subject, by using the CT image data acquired by the CT apparatus for treatment planning 100. Further, for example, the treatment planning apparatus 200 is configured to make plans about emission angles of the radiation to be emitted by the radiation therapy apparatus 400 onto the treatment target site of which the position was identified by using the CT image data, as well as a dose and the shape of an irradiated field for each of the emission angles, the number of times of the emissions, and the like. Further, the treatment planning apparatus 200 is configured to transmit the treatment plan to the radiation therapy information system 300 and the radiation therapy apparatus 400.

The radiation therapy information system 300 is configured to store therein and manage various types of information related to radiation therapies. More specifically, the radiation therapy information system 300 is configured to store therein and manage, with respect to each treatment subject, various types of information related to progress of the treatment such as the treatment plan, history information (an emission history), various types of reports, and records of statuses of the treatment subject. The radiation therapy information system 300 may be accessed from any of the apparatuses and devices connected to the network 2 and is capable of providing the managed information.

The radiation therapy apparatus 400 is configured to carry out the radiation therapy, by emitting the radiation onto the treatment subject according to the treatment plan made by the treatment planning apparatus 200. In this situation, the radiation therapy apparatus 400 according to the present embodiment is a radiation therapy apparatus capable of emitting radiation by using a FLASH irradiation method by which the radiation having an ultrahigh dose rate, which is hundreds to thousands times higher than a dose rate used in normal radiation therapies, is emitted onto a radiation irradiated region. Further, the radiation therapy apparatus 400 according to the present embodiment may emit the radiation of any of the following: an electron beam, an X-ray, a gamma ray, a proton beam, and a heavy ion beam.

Figure 2:
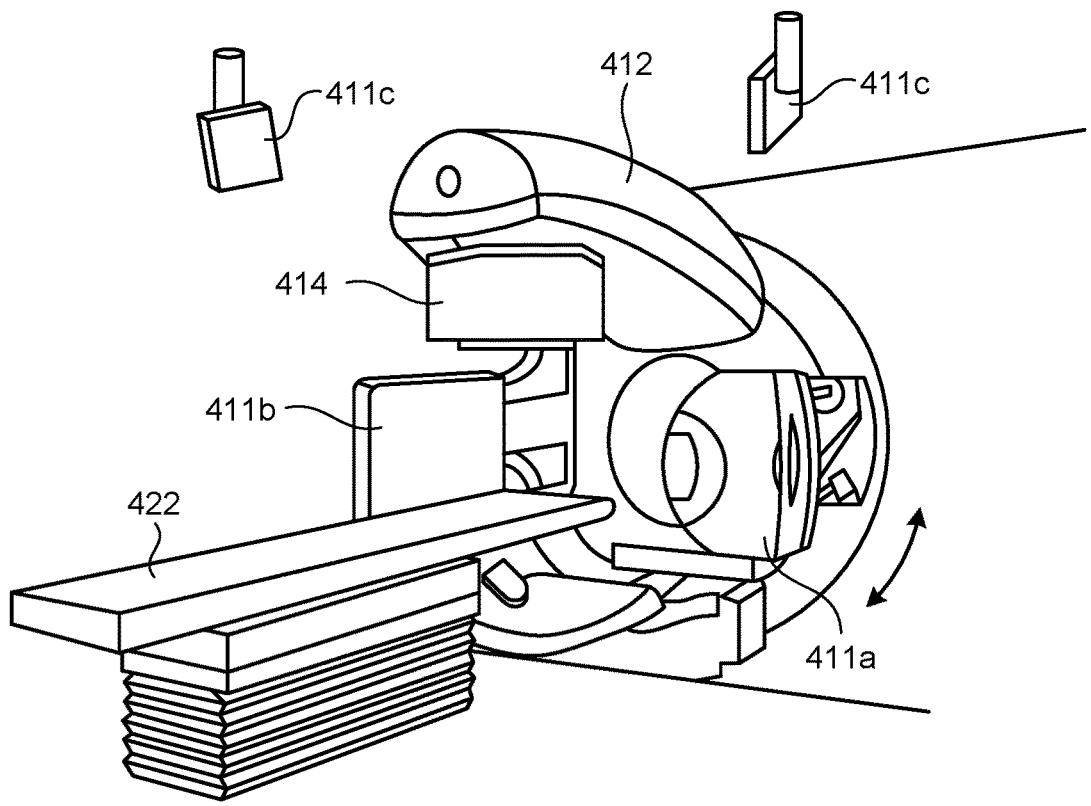
FIG. 2 is a drawing illustrating external appearance of an example of a radiation therapy apparatus according to the first embodiment.

FIG. 2 is a drawing illustrating external appearance of an example of the radiation therapy apparatus 400 according to the first embodiment. FIG. 2 illustrates the radiation therapy apparatus 400 installed in a treatment room. As illustrated in FIG. 2, the radiation therapy apparatus 400 includes: a gantry having a radiation generator 412, a collimator 414, and an imaging device (an X-ray generator 411a and an X-ray detector 411b); and a table device including a tabletop 422, and is configured to carry out the radiation therapy on the basis of control from a console (not illustrated). More specifically, the radiation therapy apparatus 400 is configured to obtain the treatment plan from the radiation therapy information system 300. Further, the radiation therapy apparatus 400 is configured to emit the radiation onto the treatment subject lying on the tabletop 422, while setting the emission angles conforming to the treatment plan by rotating the gantry in the directions indicated by the arrows.

In this situation, for the radiation therapy, the CT apparatus 100 for treatment planning at first acquires the three-dimensional CT image data necessary for making the treatment plan. On such occasion, a fixture may be created for the purpose of enhancing reproducibility and retainability of the posture of the treatment subject. Further, a marker may be attached to the body surface of the treatment subject, as required by a position alignment process performed to have the radiation emitted accurately in each session of the radiation therapy.

Further, in the treatment plan, the radiation irradiated region, the emission angles of the radiation, the dose and the shape of the irradiated field for each of the emission angles, the number of times of the emissions, and the like are determined. For example, to determine the radiation irradiated region, risk organs that need to avoid being irradiated with the radiation is set, at first, on the basis of the CT image data acquired by the CT apparatus for treatment planning 100 or the like. Further, Gross Tumor Volume (GTV) represented by a three-dimensional region in which development or the presence of a tumor is visually recognizable is set. Also, Clinical Target Volume (CTV) including the set GTV and a tumor region that is potential but is not visually recognizable is set. In this situation, the risk organs, the GTV and the CTV are set by a contouring process (an outline extraction), for example. The contouring process may be manually performed by a medical doctor or may be automatically performed by using an image processing technique.

Further, to determine the radiation irradiated region, the CTV is set with Internal Target Volume (ITV) including an internal margin (IM) used for absorbing impacts of movements of organs in the body such as respiration, swallowing, heartbeats, peristalsis, and the like. Further, the CTV is set with Planning Target Volume (PTV) including a set-up margin (SM) for each emission. The radiation irradiated region is thus determined.

When the radiation irradiated region has been determined in this manner, radiation emission conditions for the determined irradiated region is set. For example, by using the treatment planning apparatus 200, an operator (a medical worker) sets the emission conditions such as the emission angles of the radiation, the dose and the shape of the irradiated field for each of the emission angles, the number of times of the emissions, and the like. In this situation, for example, the shape of the irradiated field is formed by a Multi-Leaf Collimator (MLC) realized with the collimator 414. The MLC includes a plurality of radiation shield plates configured to set a radiation irradiated range and is capable of forming the irradiated field that matches the shape of the radiation irradiated region (PTV), as a result of the shield plates being driven independently of one another on the basis of the treatment plan.

The treatment plan generated in this manner is transmitted to the radiation therapy information system 300 and is managed together with treatment subject information, a treatment history, and the like. At the time of the radiation therapy, the treatment plan is transmitted from the radiation therapy information system 300 to the radiation therapy apparatus 400. The radiation therapy apparatus 400 is configured to emit the radiation onto the treatment subject lying on the tabletop 422, according to the received treatment plan.

In this situation, to ensure that the treatment subject lying on the tabletop 422 has the same posture as the posture assumed at the time of acquiring the treatment-planning-purpose CT image data, a rough position alignment process is performed by adjusting the posture of the treatment subject and the table so that the marker attached to the body surface of the treatment subject overlaps with a laser beam emitted from a laser designator.

After that, the radiation therapy apparatus 400 generates position-alignment-purpose cone beam CT image data, by using the imaging device including the X-ray generator 411a and the X-ray detector 411b, so as to align the position of the radiation irradiated region with an isocenter of the radiation therapy apparatus 400. For example, by causing X-rays to be emitted from the X-ray generator 411a while rotating the gantry, the radiation therapy apparatus 400 is configured to acquire projection data corresponding to an angle equal to or larger than 200 degrees and to reconstruct the cone beam CT image data, which is three-dimensional, on the basis of the acquired projection data.

The radiation therapy apparatus 400 is configured to perform the position alignment process between the irradiated region and the isocenter, by using the reconstructed cone beam CT image data and the treatment-planning-purpose CT image data. Other than the position alignment process using the cone beam CT image data described above, the radiation therapy apparatus 400 is capable of performing the position alignment process by using other methods. For example, as illustrated in FIG. 2, two X-ray imaging devices 411c may be installed in the treatment room, as imaging devices. The radiation therapy apparatus 400 may perform the position alignment process on the irradiated region and the isocenter, by causing the two X-ray imaging devices 411c to image the treatment subject lying on the tabletop 422 and comparing acquired X-ray images from the two directions with a Digitally Reconstructed Radiograph (DRR) generated from the treatment-planning-purpose CT image data. In this situation the DRR is a virtual X-ray radiography image obtained by projecting the treatment-planning-purpose CT image data into the two directions used in the imaging of the two X-ray imaging devices 411c.

As explained above, in the radiation therapy, the fine-tuned position alignment process is performed to carry out the radiation emission according to the treatment plan, while the dose and the like of the radiation emission are strictly managed. In this situation, when the radiation is emitted by implementing the FLASH irradiation method mentioned above, because the dose rate of the radiation is extremely high (e.g., hundreds to thousands times higher than normal), adjustment of a radiation emission period requires a precision level that is hundreds to thousands times higher. Further, because the dose rate of the radiation fluctuates and is not always constant, it is necessary to further adjust the radiation emission period in accordance with the fluctuation of the dose rate. In other words, according to the FLASH irradiation method, because the dose rate of the radiation being used is higher, a slight difference in the emission period greatly affects the emission dose.

For this reason, the radiation therapy apparatus 400 according to the present embodiment is configured to improve the precision level of the emission dose, by monitoring, in a real-time manner, the radiation emitted from the radiation generator and adjusting the radiation emission period on the basis of a result of the monitoring. More specifically, the radiation therapy apparatus 400 according to the present embodiment is configured to improve the precision level of the emission dose by monitoring, in a real-time manner, the dose rate and an accumulated dose of the radiation emitted from the radiation generator and stopping the radiation emission when a target dose is reached.

Figure 3:
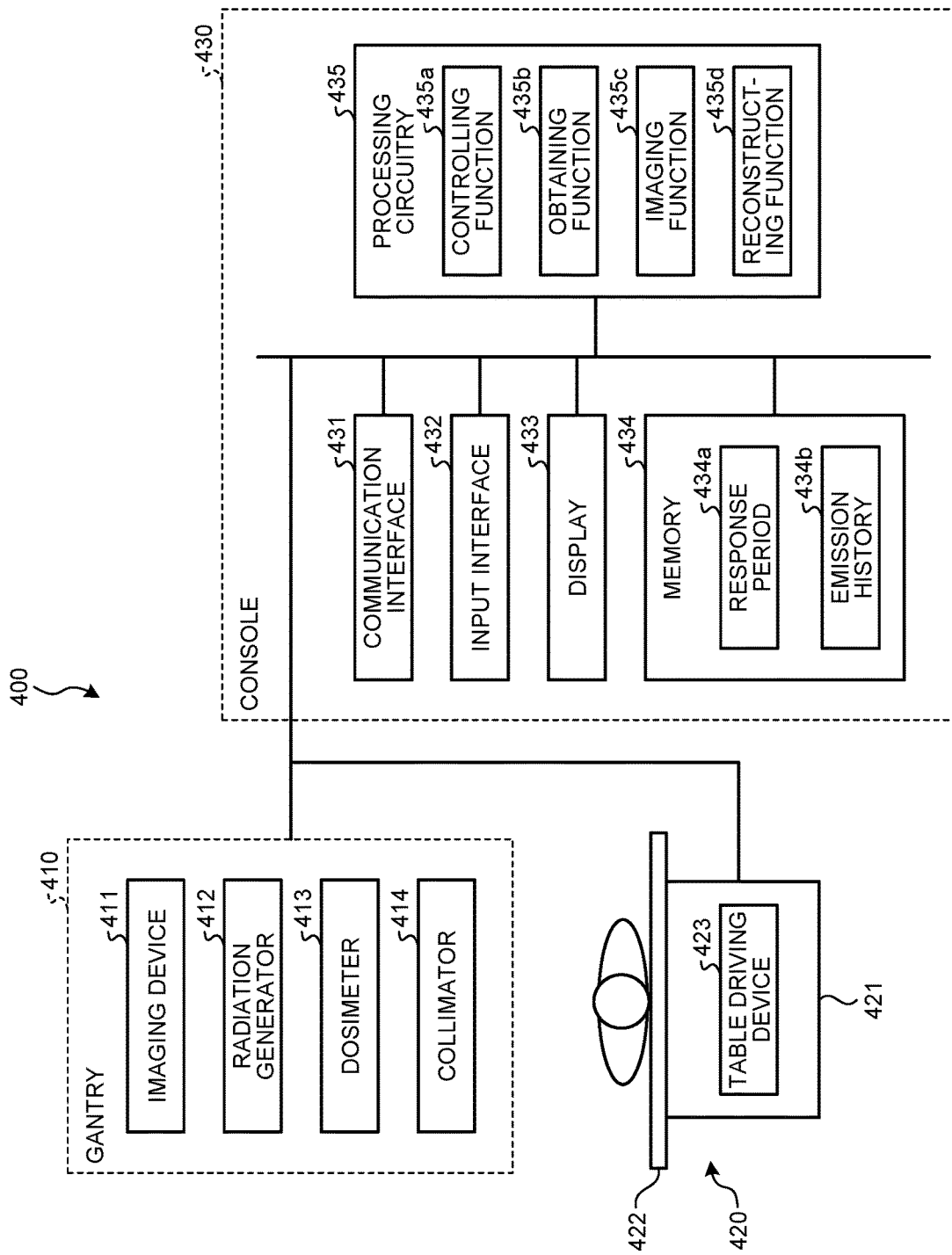
FIG. 3 is a diagram illustrating an exemplary configuration of the radiation therapy apparatus according to the first embodiment.

Next, details of the radiation therapy apparatus 400 according to the present embodiment will be explained. FIG. 3 is a diagram illustrating an exemplary configuration of the radiation therapy apparatus 400 according to the first embodiment. As illustrated in FIG. 3, the radiation therapy apparatus 400 includes a gantry 410, a table device 420, and a console 430.

The gantry 410 includes an imaging device 411, the radiation generator 412, a dosimeter 413, and the collimator 414. The imaging device 411 includes the X-ray generator 411a and the X-ray detector 411b and is configured, under control of the console 430, to image the treatment subject placed on the table device 420 to acquire the cone beam CT image data. More specifically, the imaging device 411 is arranged so that the X-ray generator 411a configured to emit the X-rays for the imaging opposes the X-ray detector 411b configured to detect the X-rays for the imaging, while the treatment subject is interposed therebetween. Further, the imaging device 411 is configured to acquire the projection data corresponding to the angle equal to or larger than 200 degrees, by causing the X-rays to be emitted from the X-ray generator 411a while the gantry 410 is rotating and causing the X-ray detector 411b to detect the X-rays. The imaging device 411 is configured to transmit the acquired projection data to the console 430.

The radiation generator 412 includes an electron gun and an acceleration tube (not illustrated). The acceleration tube is configured to emit the radiation used for the treatment, by accelerating thermo electrons generated from the electron gun so as to collide with a tungsten target. In this situation, the radiation generator 412 is capable of generating the radiation in a dose that enables radiation emission based on the FLASH irradiation method. Specifically, the radiation generator 412 emits radiation having an ultrahigh dose rate for a short period of time. For example, the radiation generator 412 emits more than 40 gray/second (Gy/sec) of radiation for the short period of time. The radiation generator 412 is an example of the emitting unit.

The dosimeter 413 is configured to measure the dose of the radiation emitted by the radiation generator 412. More specifically, the dosimeter 413 is configured to measure, over a period of time, doses of the radiation emitted by the radiation generator 412. For example, the dosimeter 413 is a dosimeter in an ion chamber (an ionization chamber) or the like, is provided between the radiation generator 412 and the collimator 414, and is configured to measure the doses of the radiation that has entered therein. The dosimeter 413 is an example of the measuring unit.

For example, the collimator 414 is the MLC and includes the plurality of radiation shield plates used for setting the radiation irradiated range for the treatment. For example, under the control of the console 430, the collimator 414 is configured to form the radiation irradiated field having the shape corresponding to the irradiated region of the treatment subject, by moving the plurality of radiation shield plates independently of one another while using a moving mechanism (not illustrated).

The table device 420 includes a pedestal 421 and the tabletop 422. The pedestal 421 has a table driving device 423 built therein and is configured to movably support the tabletop 422. The tabletop 422 has a flat shape and has the treatment subject placed thereon. The table driving device 423 includes a motor, an actuator, and the like, and is configured to move the tabletop 422 under the control of the console 430.

The console 430 includes a communication interface 431, an input interface 432, a display 433, a memory 434, and processing circuitry 435.

The communication interface 431 is connected to the processing circuitry 435 and is configured to control communication and transfer of various types of data to and from the apparatuses and devices connected via the network 2. For example, the communication interface 431 is realized by using a network card, a network adaptor, a Network Interface Controller (NIC), or the like.

The input interface 432 is connected to the processing circuitry 435 and is configured to convert input operations received from an operator (a medical worker) into electrical signals and to output the electrical signals to the processing circuitry 435. More specifically, the input interface 432 is configured to convert the input operations received from the operator into the electrical signals and to output the electrical signals to the processing circuitry 435. For example, the input interface 432 is realized by using a trackball, a switch button, a mouse, a keyboard, a touchpad on which input operations can be performed by touching an operation surface thereof, a touch screen in which a display screen and a touchpad are integrally formed, a contactless input circuit using an optical sensor, an audio input circuit, and/or the like. In the present disclosure, the input interface 432 does not necessarily have to include physical operation component parts such as a mouse, a keyboard, and/or the like. Possible examples of the input interface 432 include, for instance, an electrical signal processing circuit configured to receive electrical signals corresponding to input operations from an external input device provided separately from the apparatus and to output the electrical signals to a controlling circuit.

The display 433 is connected to the processing circuitry 435 and is configured to display various types of information and various types of image data output from the processing circuitry 435. For example, the display 433 is realized by using a liquid crystal display, a Cathode Ray Tube (CRT) display, an organic Electroluminescence (EL) display, a plasma display, a touch panel, or the like. In the present embodiment, for example, the display 433 is configured to display the treatment plan and the emission history. Further, the display 433 is configured to display information such as an emission status.

The memory 434 is connected to the processing circuitry 435 and is configured to store therein various types of data. For example, the memory 434 is realized by using a semiconductor memory element such as a Random Access Memory (RAM) or a flash memory, or a hard disk, an optical disk, or the like. In one example, the memory 434 is configured to store therein a response period 434a and an emission history 434b. Further, the memory 434 is configured to store therein the treatment plan received from the radiation therapy information system 300 and various types of processing results. Furthermore, the memory 434 is configured to store therein programs corresponding to various types of functions executed by the processing circuitry 435.

The response period 434a is response time indicating a period of time from issuance of a control signal within the apparatus, to the actual execution of control. For example, the response period 434a may be a time period from a time when a control signal (an emission stop command) to stop the emission of the radiation is transmitted to the radiation generator 412, to a time when the radiation is actually stopped.

The emission history 434b includes the emission conditions and a dose distribution of the radiation that was actually emitted onto the treatment subject and is stored into the memory 434 every time a radiation emission is carried out. The emission history 434b is transmitted to the radiation therapy information system 300 every time a radiation emission is completed so as to be managed by the radiation therapy information system 300.

The processing circuitry 435 is configured to control operations of the entirety of the radiation therapy apparatus 400 in accordance with the input operations received from the operator via the input interface 432. For example, the processing circuitry 435 is realized by using a processor. As illustrated in FIG. 3, the processing circuitry 435 is configured to execute a controlling function 435a, an obtaining function 435b, an imaging function 435c, and a reconstructing function 435d. In the present example, the controlling function 435a is an example of a controlling unit.

The controlling function 435a is configured to exercise control so that processes corresponding to various types of requests input via the input interface 432 are performed. For example, the controlling function 435a is configured to control the transmission and reception of information (e.g., the treatment plan, the emission history) performed via the communication interface 431, the storing of information into the memory 434, and the display of information on the display 433.

Further, by transmitting control signals based on the treatment plan, the controlling function 435a is configured to control the rotation of the gantry 410, the radiation emission by the radiation generator 412, the moving of the radiation shield plates included in the collimator 414, and the like. Further, by transmitting control signals based on the treatment plan, the controlling function 435a is configured to control the moving of the tabletop 422, by controlling the table driving device 423 included in the table device 420.

In the present example, the controlling function 435a is capable of controlling the radiation emission based on the FLASH irradiation method. In other words, the controlling function 435a is capable of controlling the radiation generator 412 so as to emit the radiation having a high dose rate. Further, on the basis of information about radiation doses obtained by the obtaining function 435b, the controlling function 435a is configured to calculate an accumulated dose and a dose rate of the radiation emitted from the radiation generator 412 and to control the radiation generator 412 so as to stop the radiation emission on the basis of the calculated accumulated dose and dose rate. This control will be explained in detail later.

The obtaining function 435b is configured to obtain the information about the doses measured by the dosimeter 413. More specifically, with respect to the radiation emitted from the radiation generator 412, the obtaining function 435b is configured to obtain the information about the doses measured by the dosimeter 413. For example, the obtaining function 435b is configured to obtain the information about the doses regularly measured by the dosimeter 413.

The imaging function 435c is configured to acquire the projection data used for reconstructing the cone beam CT image data, by controlling the imaging device 411. More specifically, the imaging function 435c is configured to control the rotation of the gantry 410, the X-ray emission by the X-ray generator 411a, and the data acquisition by the X-ray detector 411b. For example, the imaging function 435c is configured to acquire the projection data corresponding to the angle equal to or larger than 200 degrees around the treatment subject, by causing the X-ray generator 411a to emit the X-rays and causing the X-ray detector 411b to acquire the data, while rotating the gantry 410 by 200 degrees or larger. After that, the imaging function 435c is configured to store the acquired projection data into the memory 434.

Further, when the two X-ray imaging devices 411c are installed in the treatment room, the imaging function 435c is configured to acquire the X-ray images corresponding to the two directions by controlling the two X-ray imaging devices 411c and to store the acquired X-ray images corresponding to the two directions into the memory 434.

The reconstructing function 435d is configured to generate any of various types of images from the projection data acquired by the imaging function 435c and to store the generated images into the memory 434. For example, the reconstructing function 435d is configured to reconstruct the cone beam CT image data by reconstructing the projection data while implementing any of various types of reconstruction methods and to store the reconstructed cone beam CT image data into the memory 434.

By using the reconstructed cone beam CT image data and the treatment-planning-purpose CT image data, the controlling function 435a is configured to perform the position alignment process between the irradiated region and the isocenter and to control the emission of the radiation onto the irradiated region.

In this situation, with respect to the radiation emission based on the FLASH irradiation method, the controlling function 435a is configured to improve the precision level of the emission dose by monitoring the doses in a real-time manner and controlling the radiation emission on the basis of the monitoring result. More specifically, on the basis of the radiation doses measured over the period of time, the controlling function 435a is configured to control the radiation emission up to the time when the target dose is reached. More specifically, on the basis of the radiation doses measured over the period of time, the controlling function 435a is configured to calculate the accumulated dose and the dose rate of the radiation emitted from the radiation generator 412 and to control the dose rate of the radiation emitted until the target dose is reached, on the basis of the accumulated dose and the dose rate. For example, the controlling function 435a is configured to calculate the accumulated dose and the dose rate of the radiation emitted from the radiation generator 412 on the basis of the radiation doses measured by the dosimeter 413 and to control the radiation generator 412 so as to stop the radiation emission on the basis of the calculated accumulated dose and dose rate.

In other words, on the basis of the radiation doses measured by the dosimeter 413, the controlling function 435a is configured to calculate the accumulated dose that has been emitted onto the irradiated region and a dose per unit time period. Further, on the basis of the calculated accumulated dose and dose rate and the target dose to be emitted onto the irradiated region, the controlling function 435a is configured to judge whether or not the radiation emission is to be stopped and to stop the radiation emission on the basis of a result of the judgment.

For example, on the basis of the accumulated dose and the dose rate of the radiation, the controlling function 435a is configured to predict remaining emission information indicating one or both of: a remaining emission dose being an emission dose remaining until the target dose (a target emission dose) is reached; and a remaining emission period being a time period until the target dose is reached and is configured to control the radiation generator 412 so as to stop the radiation emission on the basis of a result of the prediction.

Figure 4:
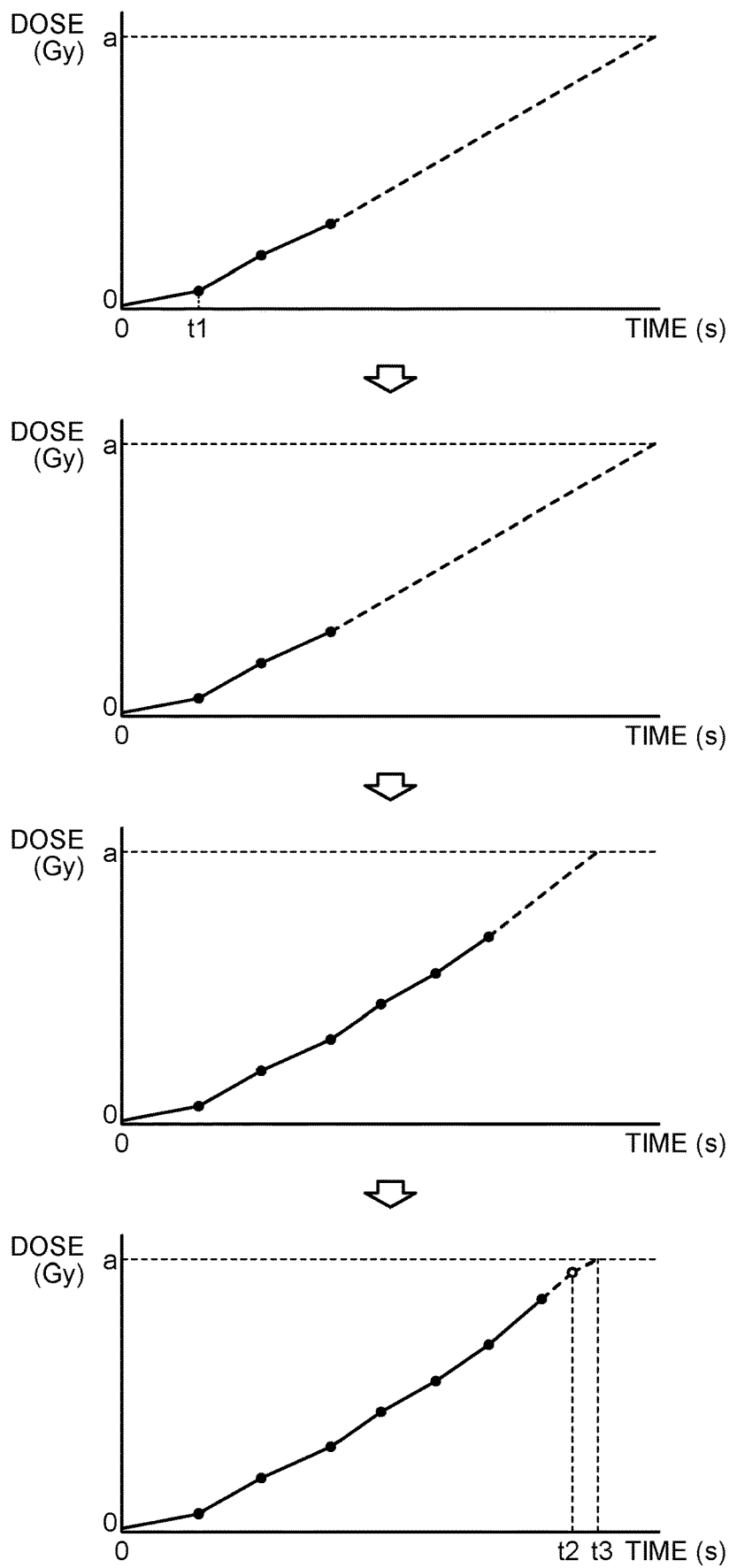
FIG. 4 presents charts for explaining control exercised by a controlling function according to the first embodiment.

FIG. 4 presents charts for explaining the control exercised by the controlling function 435a according to the first embodiment. In FIG. 4, the vertical axes express a total dose (the accumulated dose) of the radiation emitted onto the irradiated region, whereas the horizontal axes express the emission period. Further, FIG. 4 indicates values of the accumulated dose calculated on the basis of the doses measured by the dosimeter 413, by using plots with black dots. Although FIG. 4 indicates the plots with the black dots arranged at large intervals for the sake of convenience in the explanation, the doses are measured with higher frequency in actuality.

For example, as illustrated in the first chart of FIG. 4, the controlling function 435a is configured to calculate an accumulated dose, on the basis of information about the doses measured by the dosimeter 413 since the radiation emission is started. In one example, after the radiation emission is started, the controlling function 435a is configured to calculate the accumulated dose indicated by the black-dot plot in the first chart of FIG. 4, on the basis of a measurement result from the first measuring process (the measuring process at a time t1 in the chart) and a measurement result from the following measuring process. In this situation, the controlling function 435a is able to predict a remaining emission dose, from the calculated accumulated dose and the target dose ("a" in the chart). In other words, the controlling function 435a is configured to calculate the remaining emission dose by subtracting the accumulated dose from the target dose.

Further, on the basis of the doses measured by the dosimeter 413 and the time period (the radiation emission period) during which the doses were measured, the controlling function 435a is configured to calculate a dose rate of the time period. In other words, the controlling function 435a is configured to calculate the slope of the solid line in the chart of FIG. 4. In this situation, the controlling function 435a is able to predict a remaining emission period, on the basis of the calculated dose rate and the target dose ("a" in the chart). In other words, the controlling function 435a is configured to calculate the time period it will take to reach the target dose, when the emission is continued while keeping the dose rate calculated most recently (i.e., the emission indicated by the broken line in the hart chart).

In this situation, the controlling function 435a may exercise control so as to predict the remaining emission information by using radiation doses measured after a predetermined time period has elapsed since the radiation emission is started. For example, the controlling function 435a may be configured to calculate the remaining emission information without using the doses measured prior to the "time t1" indicated in the first chart of FIG. 4, but by using the measurement results thereafter. At the beginning of the radiation emission, the radiation generator 412 may have a low dose rate due to unstable outputs, in some situations. For this reason, the controlling function 435a may be configured to calculate the remaining emission information without using the information about the doses measured during such a time period, but by using the information about the doses measured after the outputs of the radiation generator 412 became stable.

In this situation, whether the outputs of the radiation generator 412 have become stable may be judged by setting the time period in advance or may be determined on the basis of doses measured by the dosimeter 413. For example, when the time period is set in advance, the controlling function 435a calculates the remaining emission information by using the certain doses measured after the time period set in advance has elapsed since the radiation emission is started. In the other example, when the judgment is based on the doses measured by the dosimeter 413, the controlling function 435a calculates a dose rate after the radiation emission is started and further determines that the outputs have become stable when the value of the dose rate exceeds a threshold value, so as to calculate the remaining emission information by using the doses measured thereafter.

Further, as indicated in the second and the third charts of FIG. 4, the controlling function 435a is configured to calculate remaining emission information as described above, every time the dosimeter 413 measures a dose (every time the obtaining function 435b obtains a measurement result). In this situation, the radiation emitted by the radiation generator 412 has a fluctuating dose rate (the slope of the solid line), as indicated by the solid-line charts in FIG.

4. The controlling function 435a is configured to monitor the changes in the dose rate in a real-time manner so as to calculate remaining emission information corresponding to the changes, at each occasion. As a result, the remaining emission dose and the remaining emission period calculated by the controlling function 435a are each information having a higher level of precision.

Further, at the time when the remaining emission information becomes equal to "0", the controlling function 435a controls the radiation generator 412 so as to stop the radiation emission. In other words, the controlling function 435a transmits a control signal to the radiation generator 412, so as to stop the radiation emission at the point in time when one of the remaining emission dose and the remaining emission period becomes equal to "0". Accordingly, the controlling function 435a is able to improve the precision level of the dose actually emitted onto the treatment subject.

In this situation, the controlling function 435a is configured to predict the remaining emission information on the basis of the accumulated dose, the dose rate, and the dose of the radiation emitted during the response time period from the point in time when the emission stop command to stop the radiation emission is issued, to the time when the radiation is stopped. There is a certain response time period (the response period) between the time when the controlling function 435a transmits the control signal and the time when the radiation emission by the radiation generator 412 actually stops. In other words, it is not that the radiation is immediately stopped at the point in time when the controlling function 435a transmits the control signal. Rather, even after the control signal is transmitted, the radiation keeps being emitted until the radiation emission is actually stopped.

For this reason, the controlling function 435a is configured to transmit the control signal to stop the radiation emission, while taking into consideration the radiation to be emitted during the abovementioned response period. More specifically, the controlling function 435a is configured to transmit the control signal to stop the radiation emission at the point in time when an accumulated dose obtained by subtracting the dose of the radiation to be emitted during the response period from the target dose is reached.

For example, as indicated in the fourth chart of FIG. 4, the controlling function 435a sets, as a temporary target dose, a value (the white-dot plot in the chart) obtained by subtracting the dose of the radiation to be emitted during the response period from the target dose "a". Further, when an accumulated dose of the radiation calculated in a real-time manner has reached the temporary target dose, the controlling function 435a transmits the control signal to stop the radiation emission. In other words, the controlling function 435a is configured to calculate the remaining emission information up to the temporary target dose and to transmit the control signal to stop the radiation emission at the point in time when the calculated remaining emission information becomes equal to "0".

In this situation, the controlling function 435a is configured to obtain the response period 434a stored in the memory 434 and to calculate a dose corresponding to the obtained response period. For example, the controlling function 435a is configured to calculate a dose to be reached when the radiation is emitted at the current dose rate for the duration (from the time t2 to the time t3 in the chart) corresponding to the response period 434a obtained from the memory 434. Further, the controlling function 435a is configured to calculate the temporary target dose by subtracting the calculated dose from the target dose. In other words, the controlling function 435a is able to appropriately set the temporary target dose, in accordance with the fluctuation of the dose rate during the radiation emission. As a result, the controlling function 435a is able to better improve the precision level of the emission dose.

The controlling function 435a is configured to store the accumulated dose emitted under the control described above, as an emission history, into the memory 434.

As explained above, the controlling function 435a is configured to monitor the doses of the radiation in the real-time manner and to control the stopping of the radiation emission on the basis of the result of the monitoring. In addition, the controlling function 435a is capable of exercising various types of control. For example, when the dose rate based on the doses measured by the dosimeter 413 is lower than a threshold value, the controlling function 435a is configured to control the radiation generator 412 so as to stop the radiation emission. In other words, when the radiation emission is carried out by implementing the FLASH irradiation method, the controlling function 435a is configured to stop the radiation emission based on the FLASH irradiation method, when the dose rate of the radiation emitted from the radiation generator 412 is greatly lower than the set value. In one example, when the dose rate of the radiation emitted from the radiation generator 412 does not satisfy a condition, the controlling function 435a stops the radiation emission based on the FLASH irradiation method, by using an interlock mechanism that prevents the radiation from being emitted.

As explained above, the controlling function 435a is configured to monitor the doses of the radiation in the real-time manner and is configured, when the condition of the dose rate according to the FLASH irradiation method is not satisfied (when the dose rate is too low for the FLASH irradiation method), to exercise control so as to stop the radiation emission based on the FLASH irradiation method. While the FLASH irradiation method is used, when the dose rate of the radiation is too low, there is a possibility of losing the advantageous characteristic where it is possible to prevent the occurrence of disturbances in normal tissues, while keeping advantageous effects on the target tissue subject to the radiation therapy. Accordingly, as a result of the controlling function 435a exercising control so as to stop the radiation emission based on the FLASH irradiation method, when the condition of the dose rate is not satisfied, it is possible to ensure higher safety and effectiveness of the radiation emission based on the FLASH irradiation method.

In this situation, when having stopped the radiation emission based on the FLASH irradiation method by using the interlock mechanism, the controlling function 435a may cause the display 433 to display certain display information indicating a status.

Further, when it is possible to change, in a real-time manner, the radiation emission output of the radiation generator 412, the controlling function 435a may change the radiation emission output of the radiation generator 412 in accordance with the dose rate based on the doses measured by the dosimeter 413. In other words, every time a dose is measured by the dosimeter 413, the controlling function 435a may exercise control so as to change the dose rate of the radiation emitted from the radiation generator 412 on the basis of a calculated dose rate. For example, when the dose rate based on the doses measured by the dosimeter 413 is lower than the threshold value, the controlling function 435a may control the radiation generator 412 so as to increase the radiation dose. In other words, while the radiation emission based on the FLASH irradiation method is carried out, the controlling function 435a is configured to exercise control so as to increase the output of the radiation generator 412 when the dose rate of the radiation emitted from the radiation generator 412 is greatly lower than the set value.

As explained above, the controlling function 435a is configured to monitor the doses of the radiation in the real-tie manner and is configured, when the condition of the dose rate based on the FLASH irradiation method is not satisfied (when the dose rate is lower than the setting), to exercise control so as to increase the radiation dose. The FLASH irradiation method has the advantageous characteristic where it is possible to prevent the occurrence of disturbances in normal tissues, while keeping the advantageous effects on the target tissue subject to the radiation therapy, by emitting the radiation in a high dose. Accordingly, as a result of the controlling function 435a exercising control so as to increase the radiation dose when the condition of the dose rate is not satisfied, it is possible to ensure higher safety and effectiveness of the radiation emission based on the FLASH irradiation method.

Figure 5:
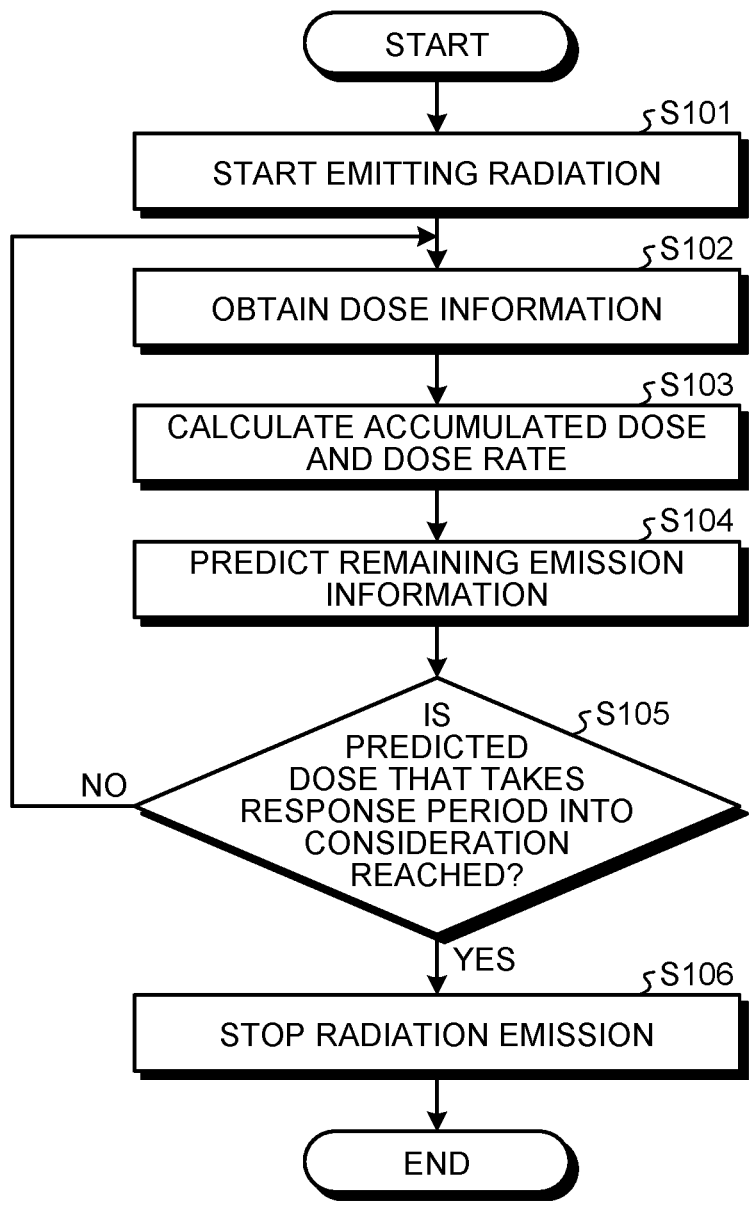
FIG. 5 is a flowchart illustrating a processing procedure performed by the radiation therapy apparatus according to the first embodiment.

Next, an example of processes performed by the radiation therapy apparatus 400 will be explained, with reference to FIG. 5. FIG. 5 is a flowchart illustrating a processing procedure performed by the radiation therapy apparatus 400 according to the first embodiment. In this situation, steps S101 and S103 through S106 in FIG. 5 are realized, for example, as a result of the processing circuitry 435 reading and executing a program corresponding to the controlling function 435a from the memory 434. Further, step S102 is realized, for example, as a result of the processing circuitry 435 reading and executing a program corresponding to the obtaining function 435b from the memory 434.

In the radiation therapy apparatus 400 according to the first embodiment, as illustrated in FIG. 5, the processing circuitry 435 starts emitting radiation (step S101) and obtains the dose information from the dosimeter 413 (step S102).

After that, the processing circuitry 435 calculates an accumulated dose and a dose rate (step S103), predicts the remaining emission information (step S104), and judges whether or not the predicted dose (the temporary target dose) taking the response period into consideration is reached (step S105).

In this situation, when the predicted dose taking the response period into consideration has not been reached (step S105: No), the processing circuitry 435 returns to step S102 and obtains dose information. On the contrary, when the predicted dose taking the response period into consideration has been reached (step S105: Yes), the processing circuitry 435 stops the radiation emission (step S106).

As explained above, according to the first embodiment, the radiation generator 412 is configured to emit the radiation. The dosimeter 413 is configured to measure, over the period of time, the doses of the radiation emitted from the radiation generator 412. On the basis of the radiation doses measured over the period of time, the controlling function 435a is configured to control the radiation emission up to the time when the target dose is reached. Consequently, the radiation therapy apparatus 400 according to the first embodiment is able to control the stopping of the radiation, by monitoring the doses of the radiation in the real-time manner and thus makes it possible to improve the precision level of the emission dose. Further, the radiation therapy apparatus 400 according to the first embodiment is capable of controlling the radiation emission up to the time when the target dose is reached by monitoring the radiation doses in the real-time manner and thus makes it possible to improve the precision level of the emission dose.

Further, according to the first embodiment, the controlling function 435a is configured to calculate the accumulated dose and the dose rate of the radiation emitted from the radiation generator 412 on the basis of the radiation doses measured over the period of time and to control the dose rate of the radiation emitted until the target dose is reached, on the basis of the accumulated dose and the dose rate. Consequently, the radiation therapy apparatus 400 according to the first embodiment is able to exercise control in accordance with the condition of the dose rate and thus makes it possible to carry out the radiation emission based on the FLASH irradiation method, while ensuring high safety and effectiveness.

Further, according to the first embodiment, on the basis of the accumulated dose and the dose rate, the controlling function 435a is configured to control the radiation generator 412 either so as to stop the radiation or so as to change the radiation dose. Consequently, the radiation therapy apparatus 400 according to the first embodiment makes it possible to exercise control in accordance with situations, with respect to the radiation emission based on the FLASH irradiation method.

Further, according to the first embodiment, on the basis of the accumulated dose and the dose rate of the radiation, the controlling function 435a is configured to predict the remaining emission information indicating one or both of: the remaining emission dose being the emission dose remaining until the target dose is reached; and the remaining emission period being the time period until the target dose is reached and is configured to control the radiation generator 412 so as to stop the radiation emission on the basis of the result of the prediction. Consequently, the radiation therapy apparatus 400 according to the first embodiment makes it possible to carry out the radiation emission with an excellent level of precision with respect to the target dose.

Further, according to the first embodiment, the controlling function 435a is configured to predict the remaining emission information on the basis of the accumulated dose, the dose rate, and the dose of the radiation emitted during the response time period from the point in time when the emission stop command to stop the radiation emission is issued, to the time when the radiation is stopped. Consequently, the radiation therapy apparatus 400 according to the first embodiment is able to carry out the radiation emission taking the response period into consideration and thus makes it possible to better improve the precision level of the emission dose.

Further, according to the first embodiment, the controlling function 435a is configured to predict the remaining emission information, by using the radiation doses measured after the predetermined time period has elapsed since the radiation emission is started. Consequently, the radiation therapy apparatus 400 according to the first embodiment is able to calculate the remaining emission information while the outputs are in a stable state and thus makes it possible to predict the remaining emission information having a high level of precision.

Further, according to the first embodiment, when the dose rate based on the doses measured by the dosimeter 413 is lower than the threshold value, the controlling function 435a is configured to control the radiation generator 412 so as to stop the radiation emission. Consequently, the radiation therapy apparatus 400 according to the first embodiment makes it possible to appropriately carry out the radiation emission based on the FLASH irradiation method. More specifically, the radiation therapy apparatus 400 according to the first embodiment is configured to exercise control so as to stop the radiation emission based on the FLASH irradiation method when the condition of the dose rate is not satisfied and thus makes it possible to ensure higher safety and effectiveness of the radiation emission based on the FLASH irradiation method.

Further, according to the first embodiment, when the dose rate based on the doses measured by the dosimeter 413 is lower than the threshold value, the controlling function 435a is configured to control the radiation generator 412 so as to increase the radiation dose. Consequently, the radiation therapy apparatus 400 according to the first embodiment makes it possible to appropriately carry out the radiation emission based on the FLASH irradiation method. More specifically, by exercising control so as to increase the radiation dose when the condition of the dose rate is not satisfied, the radiation therapy apparatus 400 according to the first embodiment is able to maintain a high dose in the radiation emission based on the FLASH irradiation method and thus makes it possible to ensure higher safety and effectiveness by maintaining a state in which the effectiveness on the target tissue is high while impacts on normal tissues are low.

Second Embodiment

In the embodiment described above, the example was explained in which the radiation emission up to the target dose is carried out with the one session of emission. As a second embodiment, an example will be explained in which the radiation emission up to the target dose is carried out through divided emissions performed in multiple divided sessions. For example, when the real-time property of the monitoring of the radiation doses is low (e.g., when the dosimeter 413 has a low responsiveness), there may be a great discrepancy between the target dose and an actual accumulated dose, when the radiation emission up to the target dose is carried out in one session of emission.

To cope with this situation, the radiation therapy apparatus 400 according to the second embodiment is configured to improve the precision level of the emission dose, by carrying out the divided emissions obtained by dividing the radiation emission into multiple sessions and changing conditions of subsequent divided emissions on the basis of emission results from the divided emissions. In this situation, the radiation therapy apparatus 400 according to the second embodiment is different from the apparatus according to the first embodiment for the control exercised by the controlling function 435a. The following sections will primarily explain the difference.

The controlling function 435a according to the second embodiment is configured to control the divided emissions performed in divided target emission doses obtained by dividing a target emission dose (the target dose) and to adjust the divided target emission dose of each divided emission, in accordance with an emission dose from already-executed divided emissions. More specifically, the controlling function 435a is configured to carry out the radiation emission with the divided emissions performed in the multiple sessions and to adjust, on the basis of an accumulated dose from the divided emissions, the target dose of the subsequent divided emissions.

Figure 6:
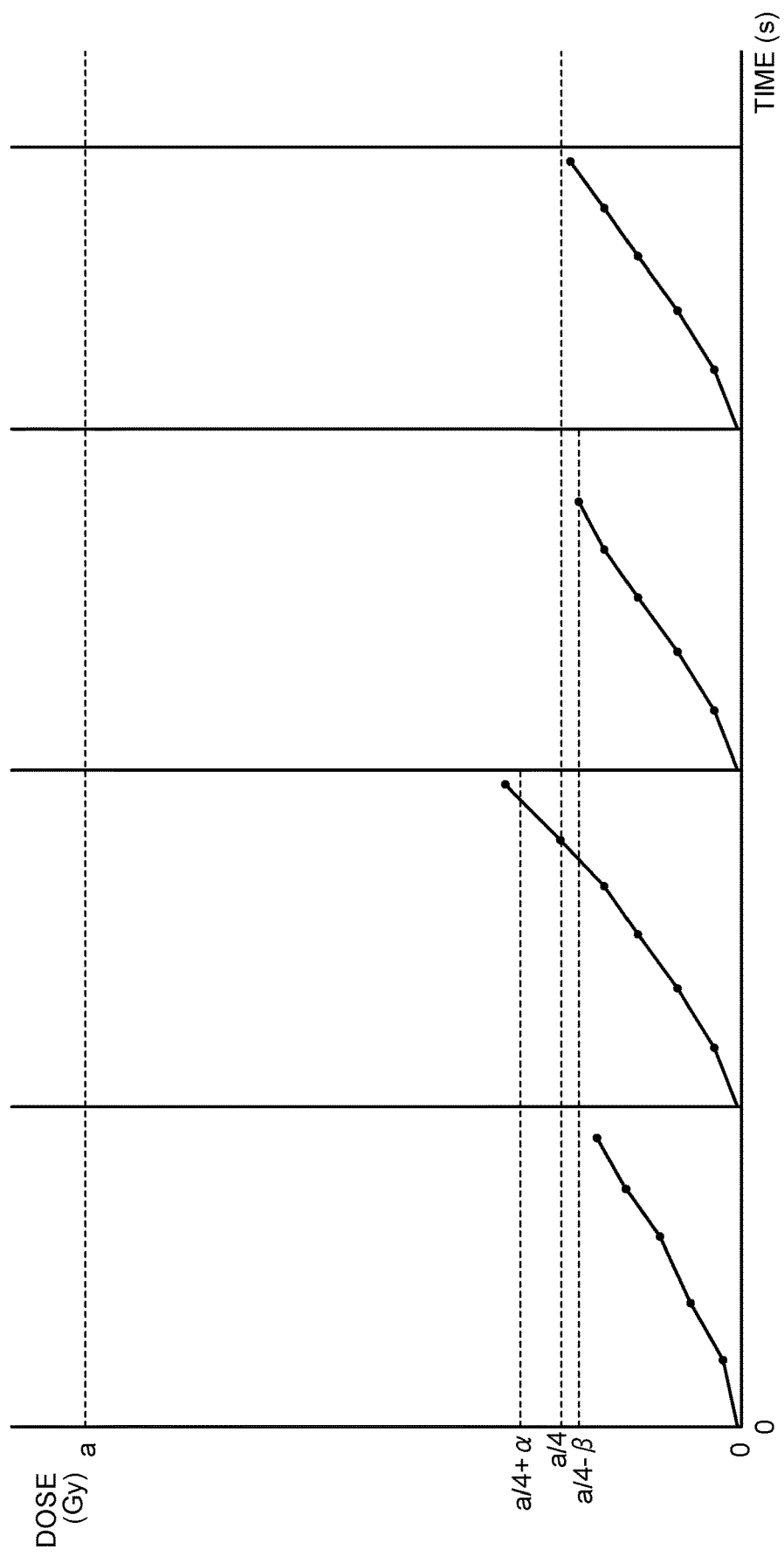
FIG. 6 is a chart for explaining control exercised by a controlling function according to a second embodiment.

FIG. 6 is a chart for explaining control exercised by the controlling function 435a according to the second embodiment. In FIG. 6, the vertical axis expresses a total dose (the accumulated dose) of the radiation emitted onto the irradiated region, whereas the horizontal axis expresses the emission period. Further, FIG. 6 indicates the values of the accumulated dose calculated on the basis of the doses measured by the dosimeter 413 by using a plot with black dots. Further, although FIG. 6 indicates the plot with the black dots arranged at large intervals for the sake of convenience in the explanation, the doses are measured with higher frequency in actuality. Further, FIG. 6 illustrates the example in which the radiation emission to emit the target dose "a" is divided into four sessions.

For example, as illustrated in FIG. 6, the controlling function 435a sets a divided target dose "a/4" obtained by dividing the radiation emission to emit the target dose "a" into the four sessions. After that, the controlling function 435a carries out a divided emission corresponding to the divided target dose "a/4". For example, as illustrated in the chart on the far left in FIG. 6, the controlling function 435a calculates, over a period of time, an accumulated dose on the basis of the doses measured during the radiation emission.

In this situation, when the real-time property is low due to responsiveness of the dosimeter 413 or the like, there may be a discrepancy between the accumulated dose at the point in time of calculation and the accumulated dose from the actual emission. To cope with this situation, the controlling function 435a is configured to judge whether or not the accumulated dose calculated on the basis of the doses measured during the radiation emission has become close to the divided target dose "a/4" and, when the judgment result is in the affirmative, to exercise control so as to stop the radiation emission.

After that, the controlling function 435a is configured to calculate an accumulated dose of the actually-emitted radiation on the basis of doses eventually measured by the dosimeter 413 and to further adjust the divided target dose of the subsequent divided emission on the basis of a result of the calculation. For example, as indicated by the chart on the far left in FIG. 6, when the accumulated dose of the actually-emitted radiation has not reached the divided target dose "a/4", the controlling function 435a adjusts the divided target dose to "a/4+α" by adding the shortage and further carries out the subsequent divided emission.

Similarly, in the subsequent divided emission also, the controlling function 435a calculates an accumulated dose of the actually-emitted radiation, on the basis of doses eventually measured by the dosimeter 413 and adjusts the divided target dose of the subsequent divided emission on the basis of a result of the calculation. For example, as indicated by the second chart from the left in FIG. 6, the controlling function 435a calculates an accumulated dose of the actually-emitted radiation, compares an accumulated dose totaling the accumulated dose from the divided emission in the first session and the accumulated dose from the divided emission in the second session, with the divided target dose "a/2" corresponding to the two sessions, and further adjusts the divided target dose of the divided emission in the third session.

In one example, the controlling function 435a compares a sum of the accumulated dose from the divided emission in the first session that did not reach the divided target dose "a/4" and the accumulated dose from the divided emission in the second session that exceeded the divided target dose "a/4+α", with the divided target dose "a/2" corresponding to the two sessions and further sets a divided target dose "a/4-β" of the divided emission in the third session.

As explained herein, the controlling function 435a according to the second embodiment is configured to divide the radiation emission into the plurality of divided emissions and to adjust the target doses of the subsequent divided emissions on the basis of the accumulated dose from each divided emission.

Figure 7:
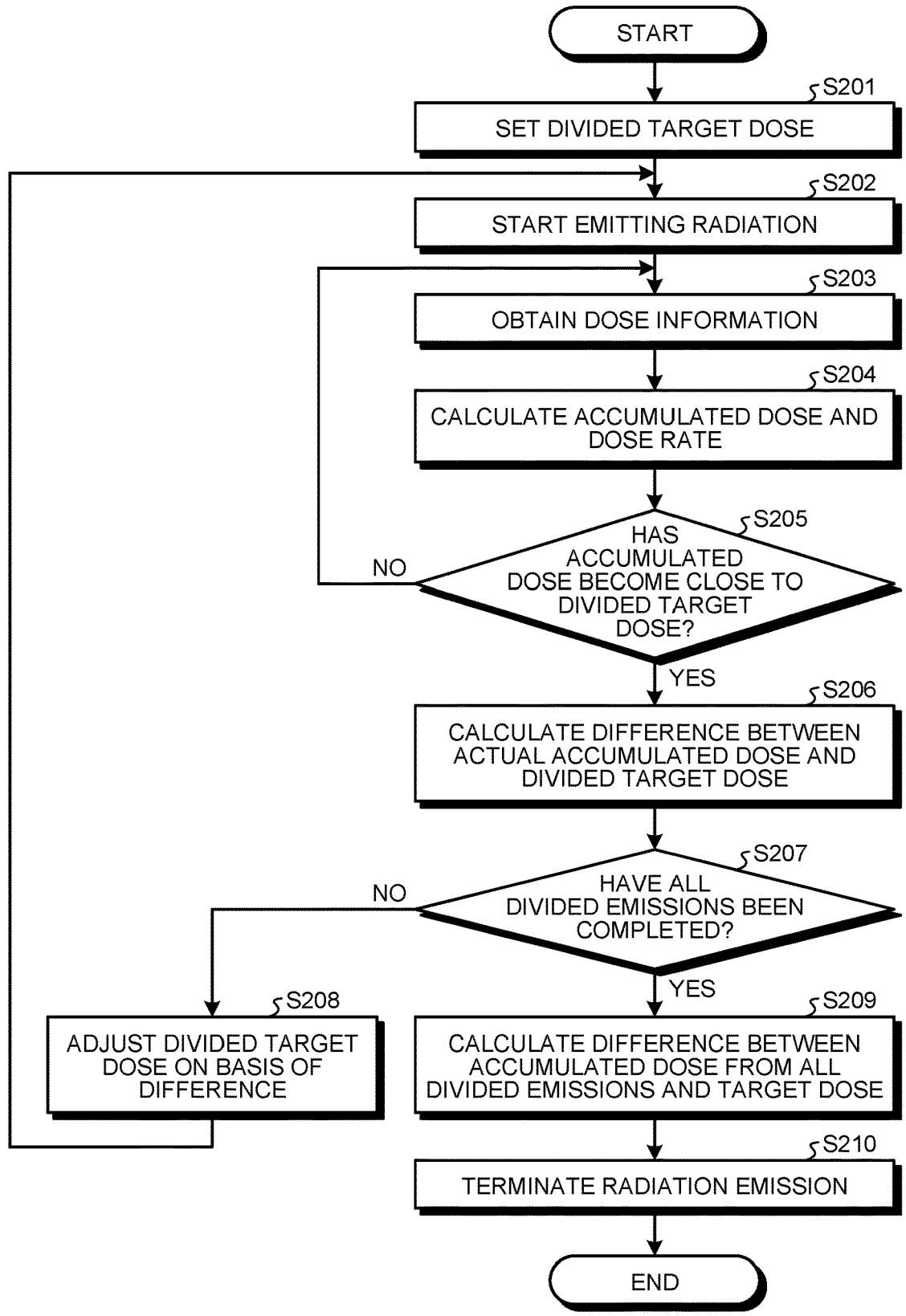
FIG. 7 is a flowchart illustrating a processing procedure performed by a radiation therapy apparatus according to the second embodiment.

Next, an example of the processes performed by the radiation therapy apparatus 400 will be explained, with reference to FIG. 7. FIG. 7 is a flowchart illustrating a processing procedure performed by the radiation therapy apparatus 400 according to the second embodiment. In the present example, steps S201, S202, and S204 through S210 in FIG. 2 are realized, for example, as a result of the processing circuitry 435 reading and executing a program corresponding to the controlling function 435*a* from the memory 434. Further, step S203 is realized, for example, as a result of the processing circuitry 435 reading and executing a program corresponding to the obtaining function 435*b* from the memory 434.

In the radiation therapy apparatus 400 according to the second embodiment, as illustrated in FIG. 7, the processing circuitry 435 sets the divided target dose (step S201) and starts emitting radiation in a divided emissions (step S202). Further, the processing circuitry 435 obtains the dose information from the dosimeter 413 (step S203), calculates an accumulated dose and a dose rate (step S204), and judges whether or not the accumulated dose has become close to the divided target dose (step S205).

In this situation, when the accumulated dose has not become close to the divided target dose (step S205: No), the processing circuitry 435 returns to step S203 and obtains dose information. On the contrary, when the accumulated dose has become close to the divided target dose (step S205: Yes), the processing circuitry 435 calculates the difference between the actual accumulated dose and the divided target dose (step S206) and judges whether or not all the divided emissions have been completed (step S207).

When all the divided emissions have not been completed (step S207: No), the processing circuitry 435 adjusts the divided target dose on the basis of the calculated difference (step S208) and returns to step S202 to start emitting the radiation. On the contrary, when all the divided emissions have been completed (step S207: Yes), the processing circuitry 435 calculates the difference between the accumulated dose from all the divided emissions and the target dose (step S209), stores an emission history, and terminates the radiation emission (step S210).

As explained above, according to the second embodiment, the controlling function 435*a* is configured to control the divided emissions performed in the divided target emission doses obtained by dividing the target emission dose and to adjust the divided emission dose of each divided emission in accordance with the emission dose from the already-executed divided emissions. Consequently, the radiation therapy apparatus 400 according to the second embodiment makes it possible to improve the precision level of the emission dose even when the real-time property is low.

Other Embodiments

The first and the second embodiments have thus been explained. However, the present disclosure may be carried out in various different modes other than those described in the first and the second embodiments.

In the embodiments described above, the example was explained in which the remaining emission information is calculated from the accumulated dose and the dose rate based on the doses measured by the dosimeter 413; however, the present disclosure is not limited to this example. For instance, the remaining emission information may be predicted by using Artificial Intelligence (AI). In that situation, for example, it is acceptable to use a trained model that has learned a relationship among temperature, humidity, and dose rates. In other words, the trained model may be generated in advance so as to use a temperature, a humidity level, and a dose rate as input data and to output a post-fluctuation dose rate, while the controlling function 435*a* is configured to predict the post-fluctuation dose rate by employing the trained model.

Figure 8:
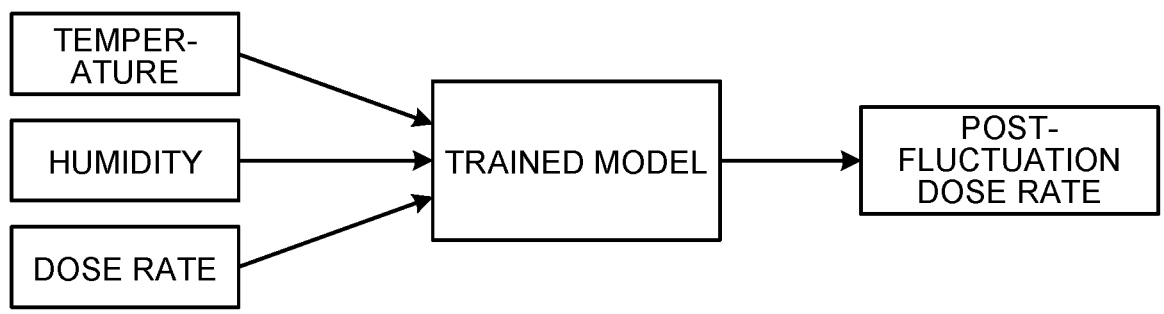
FIG. 8 is a diagram for explaining an example of a process performed by a controlling function according to another embodiment.

FIG. 8 is a diagram for explaining an example of a process performed by the controlling function 435*a* according to another embodiment. For example, the controlling function 435*a* is configured to calculate the dose rate on the basis of the doses measured by the dosimeter. After that, as illustrated in FIG. 8, the controlling function 435*a* obtains the post-fluctuation dose rate by inputting, to the trained model, temperature at the current point in time, humidity at the current point in time, and the dose rate based on the doses measured by the dosimeter. Further, the controlling function 435*a* is configured to predict remaining emission information by using the post-fluctuation dose rate. The trained model illustrated in FIG. 8 is generated in advance by learning the relationship among temperature, humidity, the dose rates, and the post-fluctuation dose rates and is stored in the memory 434.

In the embodiments above, the processing functions included in the processing circuitry 435 were explained. In this regard, for example, the processing functions described above are stored in the memory 434 in the form of computer-executable programs. The processing circuitry 435 is configured to realize the processing functions corresponding to the programs, by reading the programs from the memory 434 and executing the read programs. In other words, the processing circuitry 435 that has read the programs has the processing functions illustrated in FIG. 3.

Further, although FIG. 3 illustrates the example in which the single processing circuit (i.e., the processing circuitry 435) realizes the processing functions, possible embodiments are not limited to this example. For instance, the processing circuitry 435 may be structured by combining together a plurality of independent processors, so that the processing functions are realized as a result of the processors executing the programs. Further, the processing functions included in the processing circuitry 435 may be realized as being distributed among or integrated into one or more processing circuits, as appropriate.

Further, the term "processor" used in the above explanations of the embodiments denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). In this situation, instead of having the programs saved in the memory, it is also acceptable to directly incorporate the programs in the circuits of one or more processors. In that situation, the one or more processors are configured to realize the functions by reading and executing the programs incorporated in the circuits thereof. Further, the processors according to the present embodiments do not each necessarily have to be structured as a single circuit. It is also acceptable to structure a single processor by combining together a plurality of independent circuits, so as to realize the functions thereof.

In this situation, the programs executed by the one or more processors may be provided as being incorporated in advance in a Read-Only Memory (ROM), a storage unit, or the like. Alternatively, the programs may be provided as being stored in a computer-readable storage medium such as a Compact Disk Read-Only Memory (CD-ROM), a flexible disk (FD), a Compact Disk Recordable (CD-R), a Digital Versatile Disk (DVD), or the like, in a file that is in an installable format or in an executable format for these devices. Further, the programs may be stored in a computer connected to a network such as the Internet so as to be provided or distributed as being downloaded via the network. For example, the programs are structured by using modules including the functional units. In the actual hardware, as a result of a CPU reading and executing the programs from a storage medium such as a ROM, the modules are loaded into a main memory device, so as to be generated in the main memory device.

According to at least one aspect of the embodiments described above, it is possible to improve the precision level of the emission dose.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A radiation therapy apparatus comprising:
   radiation generator configured to emit radiation having an ultrahigh dose rate; and
   processing circuitry configured to
      measure a dose of the radiation emitted from the radiation generator over a period of time,
      calculate an accumulated dose and a dose rate of the radiation emitted from the radiation generator, on a basis of the dose of the radiation measured over the period of time,
      predict, on the basis of the accumulated dose and the dose rate of the radiation, a remaining emission period until a target dose is reached, and
      control the radiation generator so as to stop the emission of the radiation after the predicted remaining emission period has elapsed.

2. The radiation therapy apparatus according to claim 1, wherein the processing circuitry is configured to
   on the basis of the dose rate, and a response time period from a time when an emission stop command to stop the emission of the radiation is issued to a time when the radiation is stopped, calculate a response dose of radiation emitted during the response time period, and
   predict the remaining emission period, on the basis of the response dose and the accumulated dose.

3. The radiation therapy apparatus according to claim 1, wherein the processing circuitry is configured to control the radiation generator so as to stop the emission of the radiation, when the dose rate is lower than a threshold value.

4. The radiation therapy apparatus according to claim 1, wherein the processing circuitry is configured to control the radiation generator so as to increase the dose of the radiation, when the dose rate is lower than a threshold value.

5. The radiation therapy apparatus according to claim 1, wherein the processing circuitry is configured to measure, after a predetermined time period has elapsed since the radiation emission is started, the dose of the radiation over the period of time.

6. The radiation therapy apparatus according to claim 1, wherein the processing circuit is configured to
   control divided emissions performed in a divided target emission dose obtained by dividing the target dose, and
   adjust the divided target emission dose of each divided emission, in accordance with an emission dose of one or more already-executed divided emissions.

7. The radiation therapy apparatus according to claim 1, wherein the radiation generator is configured to emit more than 40 Gy/sec of radiation.

8. A radiation therapy method comprising:
   emitting radiation having an ultrahigh dose rate;
   measuring a dose of the emitted radiation over a period of time;
   calculating an accumulated dose and a dose rate of the radiation emitted from the radiation generator, on a basis of the dose of the radiation measured over the period of time;
   predicting, on the basis of the accumulated dose and the dose rate of the radiation, a remaining emission period until a target dose is reached; and
   controlling the radiation generator so as to stop the emission of the radiation after the predicted remaining emission period has elapsed.

* * * * *